United States Patent
Ro et al.

(10) Patent No.: US 11,699,072 B2
(45) Date of Patent: Jul. 11, 2023

(54) METHOD FOR VR SICKNESS ASSESSMENT CONSIDERING NEURAL MISMATCH MODEL AND THE APPARATUS THEREOF

(71) Applicant: Korea Advanced Institute of Science and Technology, Daejeon (KR)

(72) Inventors: YongMan Ro, Daejeon (KR); Hak Gu Kim, Daejeon (KR); Sangmin Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 538 days.

(21) Appl. No.: 16/700,834

(22) Filed: Dec. 2, 2019

(65) Prior Publication Data
US 2020/0327408 A1    Oct. 15, 2020

(30) Foreign Application Priority Data

Dec. 13, 2018 (KR) .................. 10-2018-0160739
Jun. 24, 2019 (KR) .................. 10-2019-0074925

(51) Int. Cl.
*G06N 3/08*      (2023.01)
*G06T 19/00*     (2011.01)
(Continued)

(52) U.S. Cl.
CPC ............ *G06N 3/08* (2013.01); *G06F 18/213* (2023.01); *G06F 18/214* (2023.01); *G06N 3/045* (2023.01);
(Continued)

(58) Field of Classification Search
CPC ........ G06N 3/08; G06N 3/0454; G06V 10/82; G06V 20/20; H04N 21/4666; G06K 9/6232; G06K 9/6256; G06T 19/006; G09B 3/06

See application file for complete search history.

(56) References Cited

U.S. PATENT DOCUMENTS 10,255,715 B2 *   4/2019   Mallinson ............ A61B 5/0531
10,565,777 B2 *   2/2020   Mallinson ............... G06T 19/20
(Continued)

FOREIGN PATENT DOCUMENTS

KR    10-2011-0139020    12/2011

OTHER PUBLICATIONS

Kim et al,, VRSA Net: VR Sickness Assessment Considering Exceptional Motion for 360° VR Video, IEEE Transactions on Image Processing, vol. 28, No. 4, Apr. 2019, pp. 1646-1660.

*Primary Examiner* — Boubacar Abdou Tchoussou
(74) *Attorney, Agent, or Firm* — Blank Rome LLP (57) ABSTRACT

A virtual reality (VR) sickness assessment method according to an embodiment includes receiving virtual reality content, and quantitatively evaluating virtual reality sickness for the received virtual reality content using a neural network based on a pre-trained neural mismatch model. The evaluating of the virtual reality sickness may include predicting an expected visual signal for an input visual signal of the virtual reality content based on the neural mismatch model, extracting a neural mismatch feature between the predicted expected visual signal based on the neural mismatch model and an input visual signal for a corresponding frame of the virtual reality content corresponding to the expected visual signal, and evaluating a level of the virtual reality sickness based on the neural mismatch model and the extracted neural mismatch feature.

18 Claims, 9 Drawing Sheets

(51) Int. Cl.

| | |
|---|---|
| *G09B 3/06* | (2006.01) |
| *G06V 20/20* | (2022.01) |
| *G06F 18/213* | (2023.01) |
| *G06F 18/214* | (2023.01) |
| *G06N 3/045* | (2023.01) |
| *G06V 10/82* | (2022.01) |
| *G06V 10/44* | (2022.01) |

(52) U.S. Cl.
CPC .......... *G06T 19/006* (2013.01); *G06V 10/454* (2022.01); *G06V 10/82* (2022.01); *G06V 20/20* (2022.01); *G09B 3/06* (2013.01)

(56) References Cited

U.S. PATENT DOCUMENTS

| | | | |
|---|---|---|---|
| 10,568,573 B2* | 2/2020 | Campbell | A61B 5/0205 |
| 10,684,469 B2* | 6/2020 | Smith | G09G 5/363 |
| 10,725,534 B2* | 7/2020 | Son | G06T 19/006 |
| 11,176,731 B2* | 11/2021 | Mallinson | A61B 5/0531 |
| 11,258,999 B2* | 2/2022 | Rao Padebettu | H04N 13/122 |
| 2017/0293356 A1* | 10/2017 | Khaderi | A61B 5/369 |
| 2018/0096244 A1* | 4/2018 | Mallinson | G06K 9/6267 |
| 2018/0096518 A1* | 4/2018 | Mallinson | G06N 5/04 |
| 2018/0256115 A1* | 9/2018 | Campbell | A61B 5/4023 |
| 2019/0171280 A1* | 6/2019 | Son | G06F 1/1686 |
| 2019/0172264 A1* | 6/2019 | Oh | G06F 3/0304 |
| 2019/0384382 A1* | 12/2019 | Hasegawa | G06T 15/20 |
| 2020/0124845 A1* | 4/2020 | Smith | G09G 5/363 |
| 2020/0183495 A1* | 6/2020 | Oh | A61B 5/742 |

* cited by examiner

METHOD FOR VR SICKNESS ASSESSMENT CONSIDERING NEURAL MISMATCH MODEL AND THE APPARATUS THEREOF

CROSS-REFERENCE TO RELATED APPLICATIONS

This application claims priority under 35 U.S.C. § 119 to Korean Patent Application No. 10-2019-0074925 filed on Jun. 24, 2019, and Korean Patent Application No. 10-2018-0160739 filed on Dec. 13, 2018, in the Korean Intellectual Property Office, the disclosures of which are incorporated by reference herein in their entireties.

BACKGROUND

Embodiments of the inventive concept described herein relate to a virtual reality (VR) sickness assessment technology, and more specifically, to a virtual reality (VR) sickness assessment method and an apparatus thereof capable of modeling the neural mismatch phenomenon that the VR sickness is felt when viewing VR content using deep learning, and quantitatively predicting the VR sickness in consideration of the modeled neural mismatch model.

Figure 1:
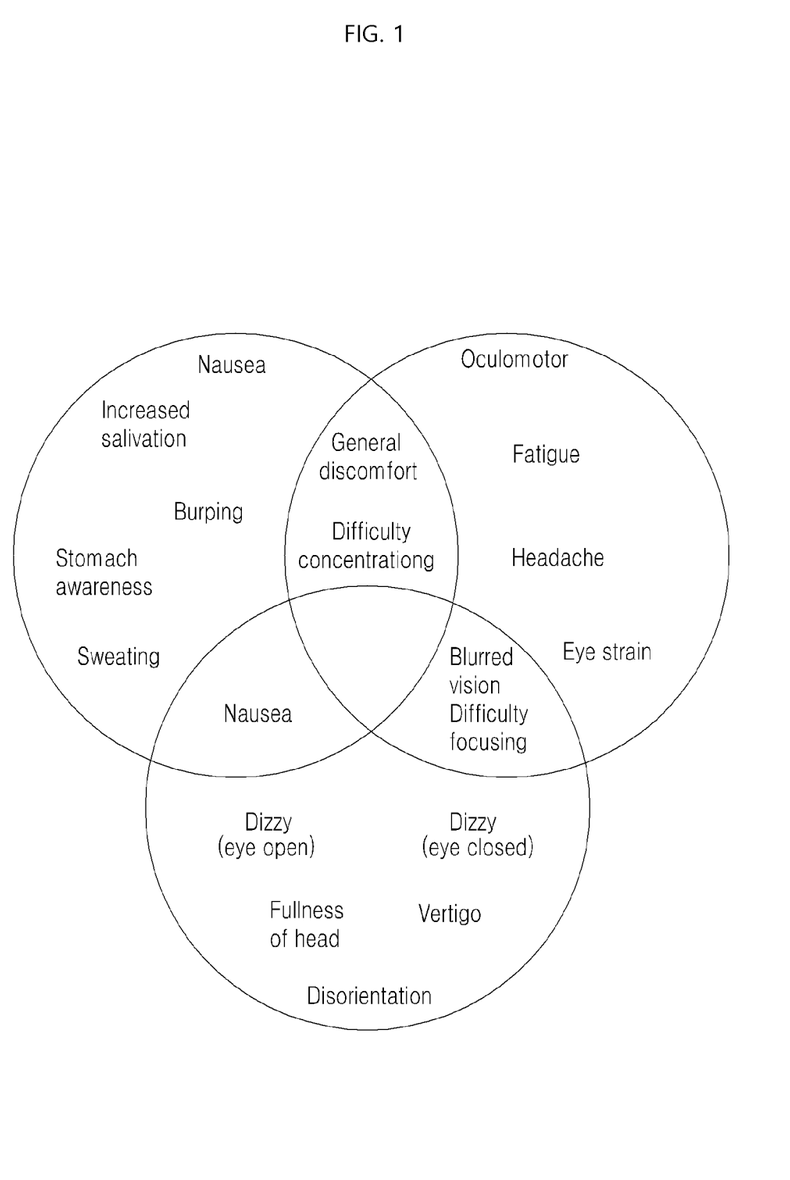
FIG. 1 is an exemplary diagram showing possible physical symptoms of VR sickness.

Virtual reality (VR) content, such as a 360-degree video, is popular due to a variety of commercial devices, such as 360-degree cameras and head-mounted displays (HMD) and unique viewing experiences, and VR recognition enables an immersive viewing experience for viewers. This is different from the 2D viewing experience. However, unwanted side effects are increasing for the safety and health of VR viewing. VR sickness that is one of motion sickness in the VR environment occurs frequently for many users exposed to VR content. Possible physical symptoms of VR sickness have been extensively studied in relation to viewing safety and health issues such as sweat, burp, visual fatigue, eye fatigue, dizziness, dizziness, and the like, and the possible physical symptoms of VR sickness include 16 major physical symptoms that can be divided into three types: oculomotor, disorientation, and nausea as examples shown in FIG. 1.

Several factors of VR sickness have been studied when watching VR content. One conventional study has investigated a display delay tolerance between a head motion and a display update (that is, delay time or latency) in a virtual environment and studied how much VR sickness is caused in various subjects while viewing the VR content due to the display delay. Another conventional study has found that, as a frame rate is lower, the level of VR sickness increases and presence decreases. Still another conventional study has investigated the effect of a low frame rate on the level of VR sickness in a virtual environment, and the experimental results showed that the low frame rate causes VR sickness. In addition, a motion (that is, a simulation motion) of the VR content may visually cause severe VR sickness. In particular, the exceptional motion patterns of the VR content leads to excessive motion mismatch, that is, vestibular mismatch between the simulation motion of the content and the user's physical motion. Still another conventional study has demonstrated that the exceptional motions of VR content have a high correlation with the level of VR sickness.

Among some theories about VR sickness, the neural mismatch model is the most appropriate theory to explain motion sickness, including VR sickness. The neural mismatch mechanism compares the converging sensory inputs of visual sensors (eyes), vestibular sensors (substrate organs and semicircular tubes), and somatosensory sensors (somatosensory receptors) with the expected sensory signals of neural stores corrected with past experience. Then, a mismatch signal, that is, a neural mismatch signal, is generated because of a mismatch between the current sensory input and the expected sensory pattern. Finally, the VR sickness is activated when the neural mismatch signal is excessive than the human perception tolerance.

Figure 2:
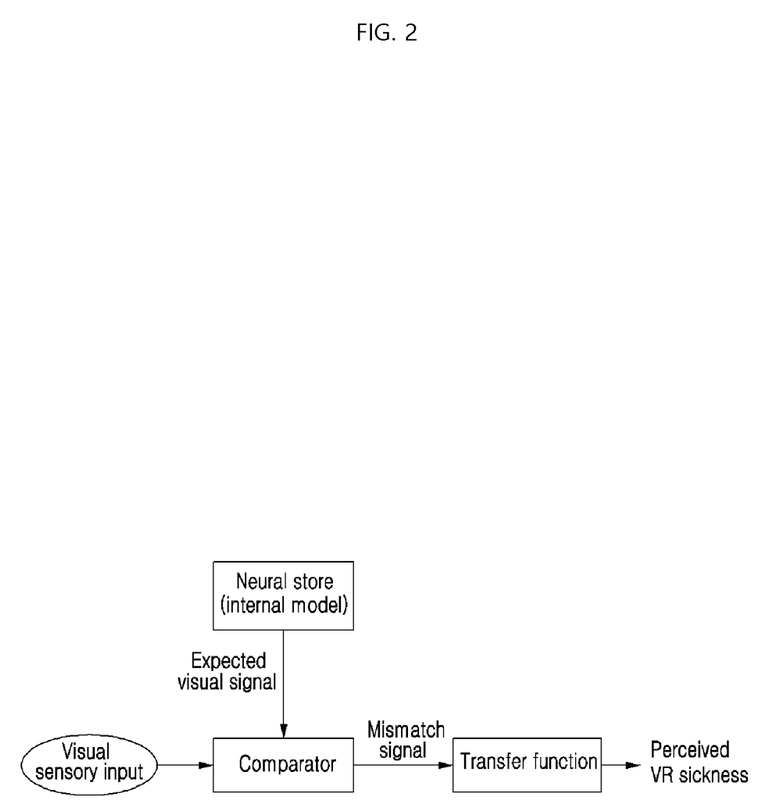
FIG. 2 shows a neural mismatch mechanism of VR sickness due to visual stimulation.

FIG. 2 illustrates a neural mismatch mechanism of VR sickness caused by visual stimulation. As shown in FIG. 2, a visual sensory input is sensed by the eyes of a user. A neural store (an internal model) may predict sensory information with past experiences learned in everyday life, such as high frame rates or general motion patterns. The comparator may compare these two signals and generate a mismatch signal. The transfer function may recognize VR sickness based on neural mismatch signals between visual sensory inputs and expected visual sensory signals.

To address the safety and soundness of VR viewing, an objective VR sickness assessment (VRSA) needs to be developed to automatically quantify the level of VR sickness. There have been many studies for evaluating VR sickness of VR content in virtual environments, and most of the conventional studies have focused on subjective assessment researches that use physiological measures and perform assessment using subjective questionnaires. One conventional technique has investigated changes in various physiological signals and the level of cybersickness for each subject, for example, correlation with the SSQ (simulator sickness questionnaire) score and for this, has measured electroencephalography (EEG), electrogastrogram (EGG), galvanic skin response (GSR), and the like. Experimental results of this technique show that there is a positive correlation between activity changes in the central nervous system and autonomic nervous system with VR sickness. Another conventional technique has measured various physiological signals of a subject during exploration of a virtual environment using HMD, and observed that physiological signals such as eye blinking, gastric activity, and breathing may be changed by sensory mismatch between the real world and the virtual world. Still another conventional technique has conducted a subjective study for measuring the quality of experience (QoE) of a 360 degree image and VR sickness by evaluating a mean opinion score (MOS) and a SSQ, respectively, but the approach using physiological measures and subjective questionnaires is very cumbersome and labor intensive, and cannot prevent viewers from watching VR content that may cause serious VR sickness.

Compared with recent studies on 2D and 3D image quality assessment (IQA) models or visual comfort assessment (VCA) for stereoscopic 3D, there are several content analytics-based VRSA methods using machine learning techniques. The conventional techniques have suggested a VR sickness predictor based on the perceptual motion feature and the statistical contents feature using support vector regression (SVR), and the predictor provides a reliable correlation with the subjective score of the human. However, there were some limitations such as the low resolution of stimulus for VR sickness, a simple five-step mean opinion score (MOS), and the like in the experimental settings. Another conventional technique has proposed a machine learning based motion sickness predictor in a 360 degree stereoscopic video to measure nausea due to VR content, and designed a regression model with less data dependence based on a decision tree using disparity and a light flow function, but have not been generalized due to the training and few test datasets. Still another conventional technique proposed a deep learning based approach considering exceptional motions of VR content, and quantified the level of VR sickness by analyzing a simulation motion using the deep learning. Experimental results of the technique showed that the proposed VRSA index is highly correlated with human subjective scores.

SUMMARY

Embodiments of the inventive concept provide a virtual reality (VR) sickness assessment method and an apparatus thereof capable of modeling the neural mismatch phenomenon that the VR sickness is felt when viewing VR content using deep learning, and quantitatively predicting the VR sickness in consideration of the modeled neural mismatch model.

According to an embodiment, a virtual reality (VR) sickness assessment method includes receiving virtual reality content, and quantitatively evaluating virtual reality sickness for the received virtual reality content using a neural network based on a pre-trained neural mismatch model.

The evaluating of the virtual reality sickness may include predicting an expected visual signal for an input visual signal of the virtual reality content based on the neural mismatch model, extracting a neural mismatch feature between the predicted expected visual signal based on the neural mismatch model and an input visual signal for a corresponding frame of the virtual reality content corresponding to the expected visual signal, and evaluating a level of the virtual reality sickness based on the neural mismatch model and the extracted neural mismatch feature.

The extracting of the neural mismatch feature may include extracting the neural mismatch feature based on difference information between the predicted expected visual signal and the input visual signal for the corresponding frame.

The extracting of the neural mismatch feature may include obtaining a difference feature for difference information between the predicted expected visual signal and the input visual signal for the corresponding frame and a visual feature for the input visual signal for the corresponding frame and extracting the neural mismatch feature based on the difference feature and the visual feature.

The evaluating of the virtual reality sickness may further include generating a difference map for the virtual reality content based on difference information between the expected visual signal predicted for each frame of the virtual reality content and the input visual signal for the corresponding frame of the virtual reality content corresponding to the expected visual signal.

The neural network may be trained based on a dataset including pieces of preset virtual reality content and a simulator sickness questionnaire (SSQ) score evaluated for each of the pieces of virtual reality content to form a learning model of the neural mismatch model.

According to an embodiment, a virtual reality (VR) sickness assessment method includes receiving virtual reality content, predicting an expected visual signal for an input visual signal of the VR content by using a first neural network based on a pre-trained first learning model, extracting a neural mismatch feature between the expected visual signal predicted and the input visual signal of a corresponding frame of the virtual reality content corresponding to the expected visual signal using a second neural network based on a pre-trained second learning model, and evaluating a level of virtual reality sickness corresponding to the extracted neural mismatch feature using a third neural network based on a pre-third trained learning model.

The extracting of the neural mismatch feature may further include extracting the neural mismatch feature based on difference information between the predicted expected visual signal and the input visual signal for the corresponding frame.

The extracting of the neural mismatch feature may further include obtaining a difference feature for difference information between the predicted expected visual signal and the input visual signal for the corresponding frame and a visual feature for the input visual signal for the corresponding frame and extracting the neural mismatch feature based on the difference feature and the visual feature.

The virtual reality sickness assessment method may further include generating a difference map for the virtual reality content based on difference information between the expected visual signal predicted for each frame of the virtual reality content and the input visual signal for the corresponding frame of the virtual reality content corresponding to the expected visual signal.

According to an embodiment, a virtual reality sickness assessment apparatus includes a receiver that receives virtual reality content, and an evaluator that quantitatively evaluates virtual reality sickness for the received virtual reality content using a neural network based on a pre-trained neural mismatch model.

According to another embodiment, a virtual reality sickness assessment apparatus includes a receiver that receives virtual reality content, a predictor predicts an expected visual signal for an input visual signal of the VR content by using a first neural network based on a pre-trained first learning model, an extractor extracts a neural mismatch feature between the expected visual signal predicted and the input visual signal of a corresponding frame of the VR content corresponding to the expected visual signal using a second neural network based on a pre-trained second learning model, and an evaluator evaluates a level of virtual reality sickness corresponding to the extracted neural mismatch feature using a third neural network based on a pre-third trained learning model, wherein a neural mismatch model is formed by the first learning model, the second learning model, and the third learning model.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Advantages and features of the inventive concept and methods for achieving them will be apparent with reference to embodiments described below in detail in conjunction with the accompanying drawings. However, the inventive concept is not limited to the embodiments disclosed below, but can be implemented in various forms, and these embodiments are to make the disclosure of the inventive concept complete, and are provided so that this disclosure will be thorough and complete and will fully convey the scope of the invention to those of ordinary skill in the art, which is to be defined only by the scope of the claims.

The terminology used herein is for the purpose of describing particular embodiments only and is not intended to be limiting of the inventive concept. The singular expressions include plural expressions unless the context clearly dictates otherwise. In this specification, the terms "comprises" and/or "comprising" are intended to specify the presence of stated components, steps, operations and/or elements, but do not preclude the presence or addition of one or more other components, steps, operations and/or elements.

Unless defined otherwise, all terms (including technical and scientific terms) used herein have the same meanings as commonly understood by one of ordinary skill in the art to which this invention belongs. Further, unless explicitly defined to the contrary, the terms defined in a generally-used dictionary are not ideally or excessively interpreted.

Hereinafter, preferred embodiments of the present invention will be described in detail with reference to the accompanying drawings. The same reference numerals are used for the same components in the drawings, and duplicate descriptions of the same components are omitted.

VR sickness is a major difficulty in watching VR. It may be explained by a neural mismatch model. The mismatch between input sensory signals by sensed by receptors and expected sensory signals predicted by a neural store with the past experience may lead to VR sickness.

Embodiments of the inventive concept are intended to quantitatively assess virtual reality sickness in consideration of a neural mismatch model obtained by modeling the phenomenon in which motion sickness is caused by the mismatch between an input sensory signal sensed when viewing VR content and an expected sensory signal predicted by the neural store with the past experience.

The inventive concept may include a neural store module that predicts visual sensory information based on past experience information, for example, a deep neural store network, a comparison module that extracts a mismatch feature between actual incoming visual information and expected visual information predicted by the neural store network, for example, a deep comparison network, and a VR sickness prediction module that predicts a level of VR sickness from the neural mismatch feature, for example, a deep VR sickness score prediction network.

The deep neural store network may predict the next frame (expected visual signal) from past experiences (that is, trained parameters in training) and train the deep neural store network with normal video that is readily available every day. In other words, by training the deep neural store network with VR videos that may not cause severe VR sickness, the deep neural store network may be trained with the spatiotemporal characteristics of normal visual signals. The deep comparison network is to compare an input video frame (that is, an input visual signal) with an expected video frame predicted by the trained deep neural store network. By encoding the mismatch between the input visual signal and the expected visual signal, the neural mismatch feature is encoded in the deep comparison network. Finally, the VR sickness score prediction network is to evaluate a VR sickness score by mapping the encoded neural mismatch feature onto a subjective score.

That is, the inventive concept may allow a VRSA framework to reliably predict the level of VR sickness caused by other factors such as an exceptional motion and a low frame rate.

Figure 3:
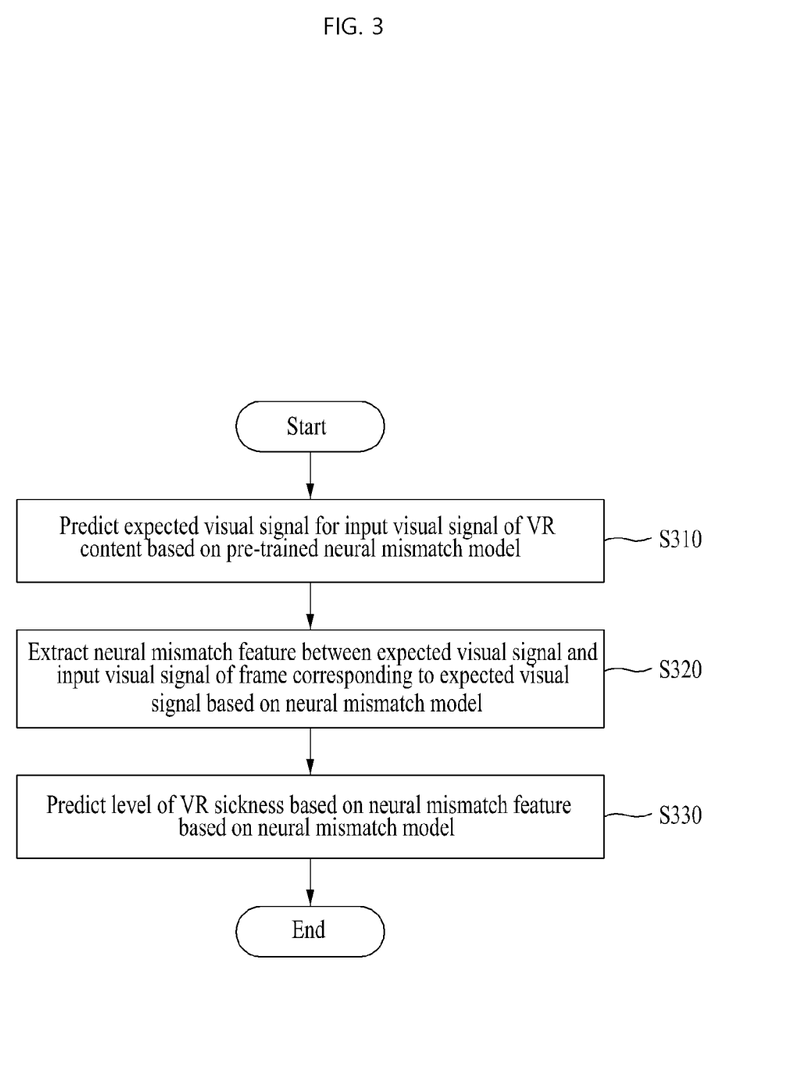
FIG. 3 is a flowchart of an operation of a virtual reality sickness assessment method according to an embodiment of the inventive concept.

FIG. 3 is a flowchart of an operation of a VR sickness assessment method according to an embodiment of the inventive concept.

Referring to FIG. 3, in a VR sickness assessment method according to an embodiment of the inventive concept, when VR content to be evaluated for VR sickness is received, an expected visual signal for an input visual signal of the VR content is predicted based on a pre-trained neural mismatch model (S310).

Here, in step S310, the expected visual signal for the input visual signal of the VR content may be predicted using a neural network based on a first learning model trained by preset training data, for example, a deep neural store network.

When the expected visual signal is predicted in the step S310, a neural mismatch feature between the expected visual signal and the input visual signal of a corresponding VR content frame corresponding to the expected visual signal may be extracted based on the neural mismatch model (S320).

Here, in step S320, a neural mismatch feature between the expected visual signal and the input visual signal of the corresponding VR content frame corresponding to the expected visual signal may be extracted by using a neural network based on a second learning model trained by preset training data, for example, a deep comparison network.

Furthermore, in step S320, the neural mismatch feature may be extracted based on a difference feature corresponding to the difference information between the input visual signal of the corresponding frame and the expected visual signal of the corresponding frame, or the neural mismatch feature may be extracted based on the visual feature for the input visual signal of the corresponding frame and the difference feature corresponding to the difference information between the input visual signal of the corresponding frame and the expected visual signal of the corresponding frame.

When the neural mismatch feature of the VR content is extracted in step S320, the VR sickness information for the corresponding VR content is quantitatively evaluated or predicted based on the neural mismatch feature based on the neural mismatch model (S330).

Here, in step S330, the VR sickness score of the VR content corresponding to the neural mismatch feature may be predicted using a neural network, for example, a deep VR sickness score prediction network based on a third learning model trained by preset training data.

The neural mismatch model may be formed by the first to third learning models, and may mean a model formed by three networks.

That is, the inventive step may evaluate a VR sickness score for VR content using one neural network based on the neural mismatch model, or evaluate the VR sickness score for the VR content by using three neural networks based the first learning model, the second learning model, and the third learning model corresponding to the neural mismatch model.

Furthermore, a method according to an embodiment of the inventive concept may generate a difference map for VR content based on the difference information between the expected visual signal predicted for each frame of the VR content and the input visual signal for a corresponding frame of the VR content corresponding to the expected visual signal, and also provide the generated difference map for the VR content.

A VR sickness assessment method according to an embodiment of the inventive concept will be described in detail with reference to FIGS. 4 to 7.

Figure 4A:
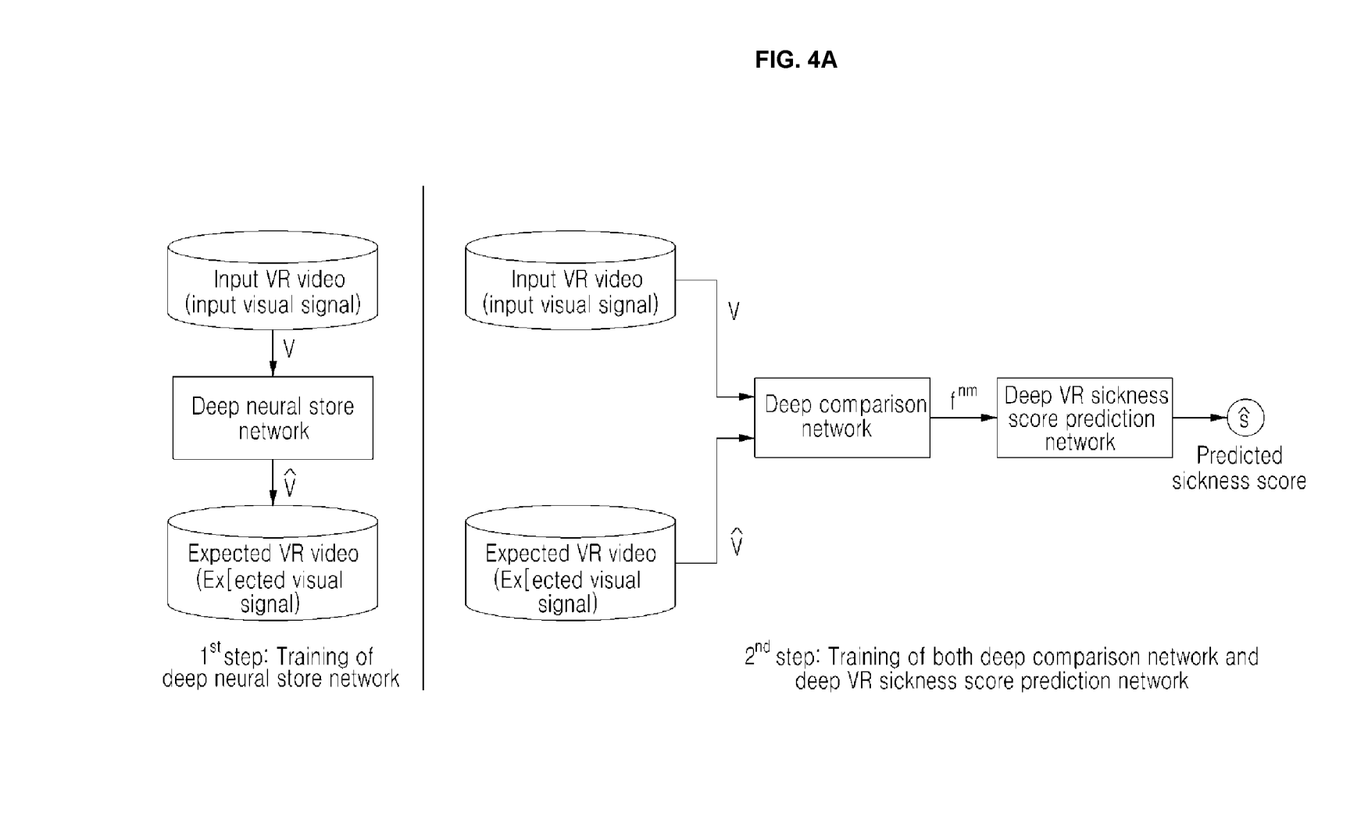
FIGS. 4A-B illustrate an overall process of VR sickness assessment in consideration of the neural mismatch in training and testing in the virtual reality sickness assessment method according to an embodiment of the inventive concept.
Figure 4B:
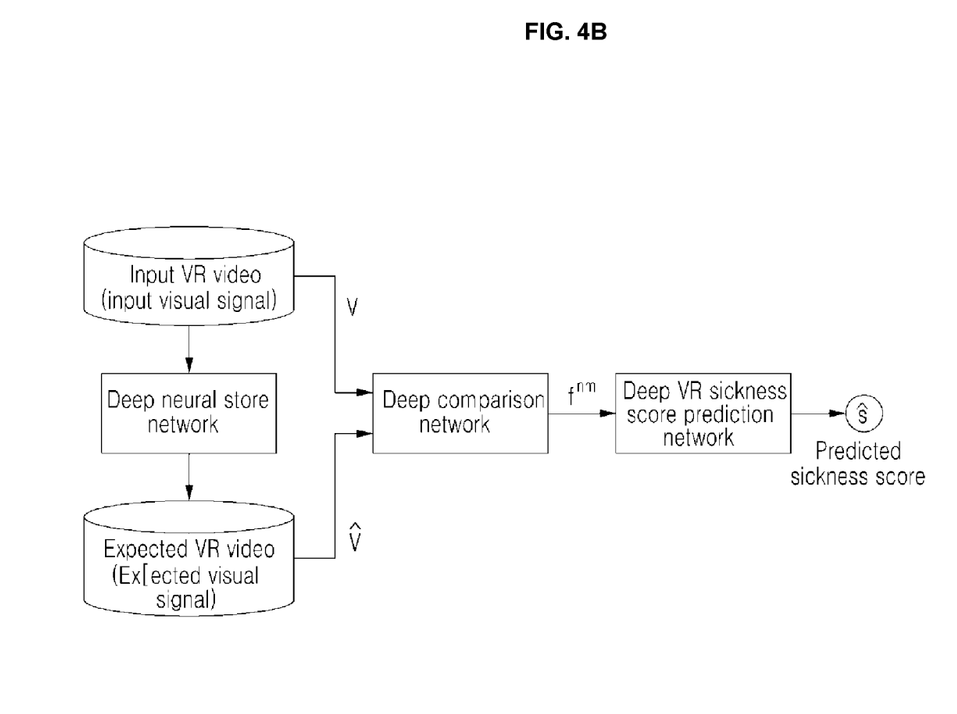

FIG. 4 is a diagram illustrating an overall process of VR sickness assessment in consideration of neural mismatch in training and test for a virtual reality sickness assessment method according to an embodiment of the inventive concept, V and $\hat{V}$ representing an input VR video and an expected VR video respectively, $f^{nm}$ representing a neural mismatch feature that learns a difference between V and $\hat{V}$, and $\hat{S}$ representing a predicted VR sickness score.

As shown in FIG. 4, the VR sickness assessment (VRSA) framework of the inventive concept may include a deep neural store network, a deep comparison network, and a deep VR sickness score prediction network.

FIG. 4A illustrates a training process of the VRSA framework of the inventive concept, and as shown in FIG. 4A, the training of the deep VRSA framework may consist of two stages of a process of training the deep neural store network and a process of training the deep comparison network and the deep VR sickness score prediction network. In the process of training the deep neural store network, the deep neural store network may learn visual signal prediction from an input visual signal. In this case, the deep neural store network may be trained with a normal video dataset with a non-exceptional motion pattern and a high frame rate to learn experience in everyday life. In other words, these features of the training dataset cannot lead to VR sickness.

FIG. 4B illustrates the testing process of the VRSA framework of the inventive concept, in which, as shown in FIG. 4B, a level of VR sickness may be predicted by the deep network trained in a test. First, each frame may be predicted by the trained deep neural store network. The deep neural store network is trained with a normal video that cannot lead to VR sickness, so that the trained network may sufficiently predict the non-exceptional motion pattern and the normal video of the high frame rate. On the other hand, exceptional motion patterns, such as VR video with acceleration and rapid turning or a low frame rate, cannot be well predicted by the trained deep neural store network because the deep neural store network does not experience such video during training. The deep comparison network may encode the difference information between the original video and the predicted video sequence into a neural mismatch feature. The deep VR sickness score prediction network ma predict a VR sickness score by mapping the neural mismatch feature onto a subjective VR sickness score.

In the inventive concept, a total SSQ score obtained by a subject may be used as a ground truth VR sickness score.

Figure 5:
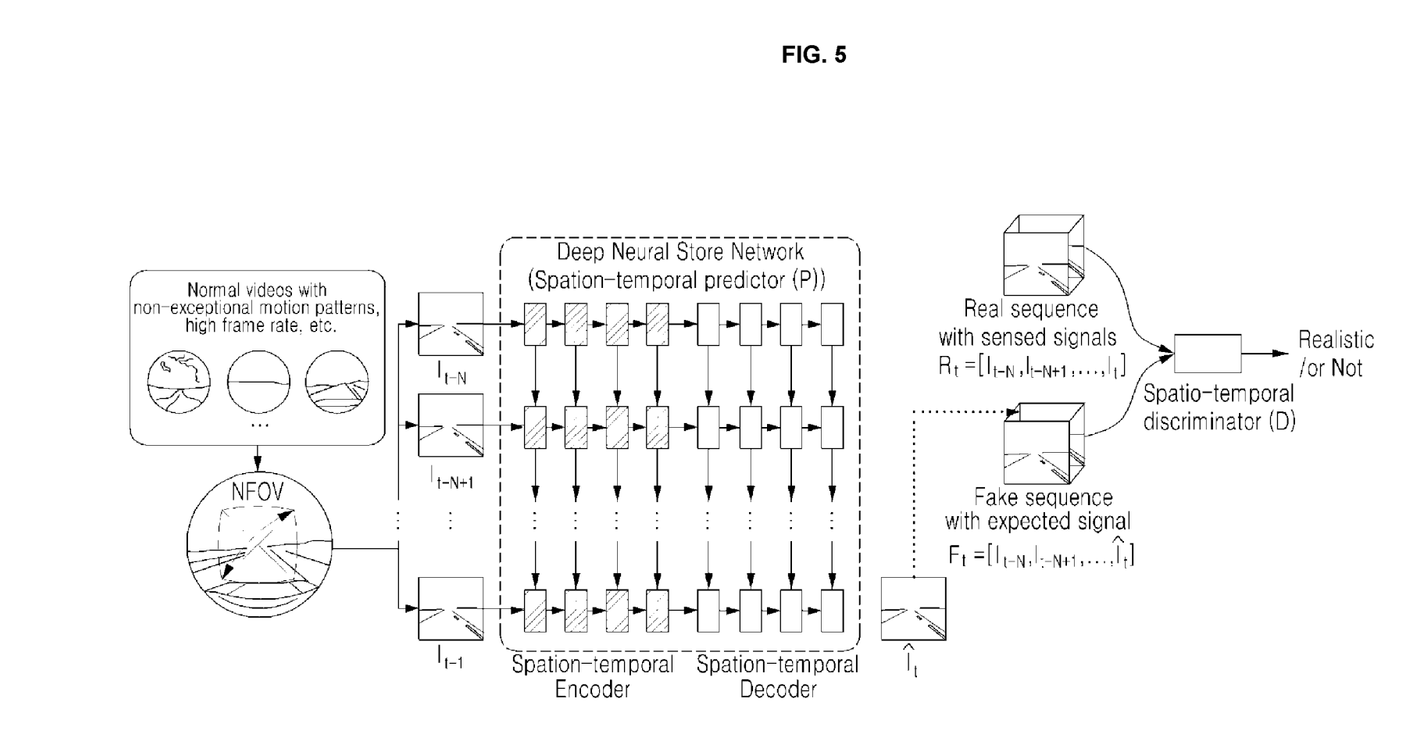
FIG. 5 illustrates an architecture of one embodiment for a neural store network using a deep generation model.

FIG. 5 illustrates an architecture of an embodiment for a neural store network using a deep generation model, where the deep neural store network may be trained with normal videos that cannot cause severe VR sickness to store everyday experiences, the yellow box represents convolutional LSTM (ConvLSTM), the blue box represents deconvolutional LSTM (DeconvLSTM) and the green box represents 3D convolutional neural network (CNN).

As shown in FIG. 5, the deep neural store network may include a spatio-temporal predictor P for prediction of the next frame and a spatio-temporal discriminator D for improving the prediction performance of the predictor. The spatio-temporal predictor P may predict the next frame in an input video sequence during training. Because people typically cannot experience situations such as low frame rates and exceptional movements that cause severe VR sickness, the deep neural store network may be also trained with non-exceptional motions and normal video sequences with high frame rates. In general, non-exceptional motions, such as static and slow progression and high frame rates, for example, a normal VR video with more than 30 frames per second (fps) may not cause severe VR sickness and their SSQ scores may be about 30 points or less. On the other hand, the SSQ scores of exceptional motions, for example, videos of a roller coaster, racing, or a low frame rate such as 10 fps or 15 fps may be 40 points or more. The inventive concept may use normal videos in which there is no exceptional motions and low frame rates to train the deep neural store network with people's general experiences. The spatio-temporal discriminator D may analyze an original video or an expected video and then determine whether the given video has a distribution of the original normal video. In an alternative way between the predictor P and the discriminator D, the deep neural store network may predict a video sequence based on trained parameters, for example, stored experiences.

The inventive concept may use, as an input frame, a normal field of view (NFOV) segment that looks comfortable from an infinite field of view (IFOV) of a 360 degree video. The NFOV may be obtained through the equirectangular projection around the field of view. The size of an NFOV area may be set over a 110-degree diagonal FOV, as with a high end HMD. When $I_t$ and $\hat{I}_t$ are respectively the t-th input frame and the t-th reconstructed frame, $V_t$ and $\hat{V}_t$ may denote the original NFOV video frame set, that is, $V_t=[I_{t-N}, \ldots, I_t]$ and the generated NFOV video frame set, that is $\hat{V}_t=[\hat{I}_{t-N}, \ldots, \hat{I}_t]$, respectively. Here, N may be 10.

The predictor of the deep neural store network consists of a spatio-temporal encoder using convolutional LSTM (ConvLSTM) and a spatio-temporal decoder using deconvolutional LSTM (DeconvLSTM).

TABLE 1

| Layer | Filter/Stride | Output size (W × H × C) |
| --- | --- | --- |
| ConvLSTM 1 | 3 × 3/(2, 2) | 112 × 112 × 16 |
| ConvLSTM 2 | 3 × 3/(2, 2) | 56 × 56 × 32 |
| ConvLSTM 3 | 3 × 3/(2, 2) | 28 × 28 × 64 |
| ConvLSTM 4 | 3 × 3/(2, 2) | 14 × 14 × 128 |
| DeconvLSTM 1 | 3 × 3/(2, 2) | 28 × 28 × 64 |
| DeconvLSTM 2 | 3 × 3/(2, 2) | 56 × 56 × 32 |
| DeconvLSTM 3 | 3 × 3/(2, 2) | 112 × 112 × 16 |
| DeconvLSTM 4 | 3 × 3/(2, 2) | 224 × 224 × 3 |

TABLE 2

| Layer | Filter/Stride | Output size (D × W × H × C) |
| --- | --- | --- |
| 3D Conv 1 | 5 × 5 × 5/(1, 2, 2) | 7 × 112 × 112 × 32 |
| 3D Conv 2 | 3 × 5 × 5/(1, 2, 2) | 5 × 56 × 56 × 64 |
| 3D Conv 3 | 3 × 3 × 3/(1, 2, 2) | 3 × 28 × 28 × 128 |
| 3D Conv 4 | 3 × 3 × 3/(1, 2, 2) | 1 × 14 × 14 × 256 |

TABLE 2-continued

| Layer | Filter/Stride | Output size (D × W × H × C) |
|---|---|---|
| 3D Conv 5 | 1 × 3 × 3/(1, 2, 2) | 1 × 7 × 7 × 1 |
| 64-d fc layer | — | 1 × 1 |

Table 1 and Table 2 above show layers, filters/strides, and output sizes for the architectures of the spatio-temporal predictor and spatio-temporal discriminator, respectively, wherein the encoder may consist of four layers of ConvLSTM for encoding the spatio-temporal feature of an input video sequence, and the decoder may also consist of four layers of DeconvLSTM for generating the next frame. In the DeconvLSTM, convolutional layers of the ConvLSTM may be replaced with deconvolutional layers to decode encoded features. All layers have a 3×3 filter size on 2 strides. The t-th predicted frame may be defined as in Equation 1 below.

$$\hat{I}_t = P_\theta(I_{t-N}, \ldots, I_{t-1}) \quad \text{[Equation 1]}$$

where $P_\theta$ may mean a predictor having a parameter $\theta$.

The predictor P may cheat the discriminator D by reconstructing a normal video sequence (e.g., non-exceptional motion or high frame rate) through hostile learning. To achieve this object, the inventive concept may design a loss function of the predictor using prediction loss and realism loss. It is possible to improve prediction quality by minimizing the prediction loss between an original frame $I_t$ and an expected frame $\hat{I}_t$. The realism loss may cause the predicted frame to be realistic enough to cheat the discriminator. Finally, the total loss LP of the spatio-temporal predictor may be defined as the sum of the prediction loss and the realism loss, and may be expressed as Equation 2 below.

$$L_P(\theta, \phi) = \|P_\theta(I_{k-N}, \ldots, I_{k-1}) - I_k)\|_2^2 - \lambda_a \log(D_\phi F_t)) \quad \text{[Equation 2]}$$

where $D_\phi$ may denote a discriminator with a parameter $\phi$, $\lambda_a$ may denote a weighting parameter that adjusts the balance between the first term for prediction and the second term for realism, and $F_t$ may denote a fake sequence containing the predicted frame.

The discriminator D may determine whether the input video is realistic in consideration of the spatio-temporal feature. As can be seen in FIG. 5, in training, the discriminator D may take a real sequence, or a fake sequence that includes a predicted frame. Then, a 1×1 output value may be created to determine whether it is real or fake. As can be seen from Table 2, the spatio-temporal discriminator D may be based on a 3D CNN structure. Here, $L_D$, which is a discriminator loss, may be expressed as Equation 3 below.

$$L_D(\phi) = \log(1 - D\phi(F_t)) + \log(D\phi(R_t)) \quad \text{[Equation 3]}$$

where $D_\phi(F_t)$ may denote the probability that the discriminator discriminates a fake sequence as the original video, and $D_\phi(R_t)$ may mean the probability that the discriminator discriminates an actual sequence as the original video.

In the inventive concept, the predictor $P_\theta$ and the discriminator $D_\phi$ may form a generative adversarial network (GAN). To train a deep neural store network including a predictor and a discriminator for hostile learning, the inventive concept may devise a new hostile objective function, which may be expressed as Equation 4 below.

$$\min_P \max_D V(P_\theta, D_\phi) := L_P(\theta, \phi) + \lambda_D L_D(\phi) \quad \text{[Equation 4]}$$

where $\lambda_D$ may denote a weighting parameter for the discriminator.

By the hostile learning between the predictor $P_\theta$ and the discriminator $D_\phi$, the prediction performance of the deep neural store network for the normal video sequence may be improved.

Figure 6:
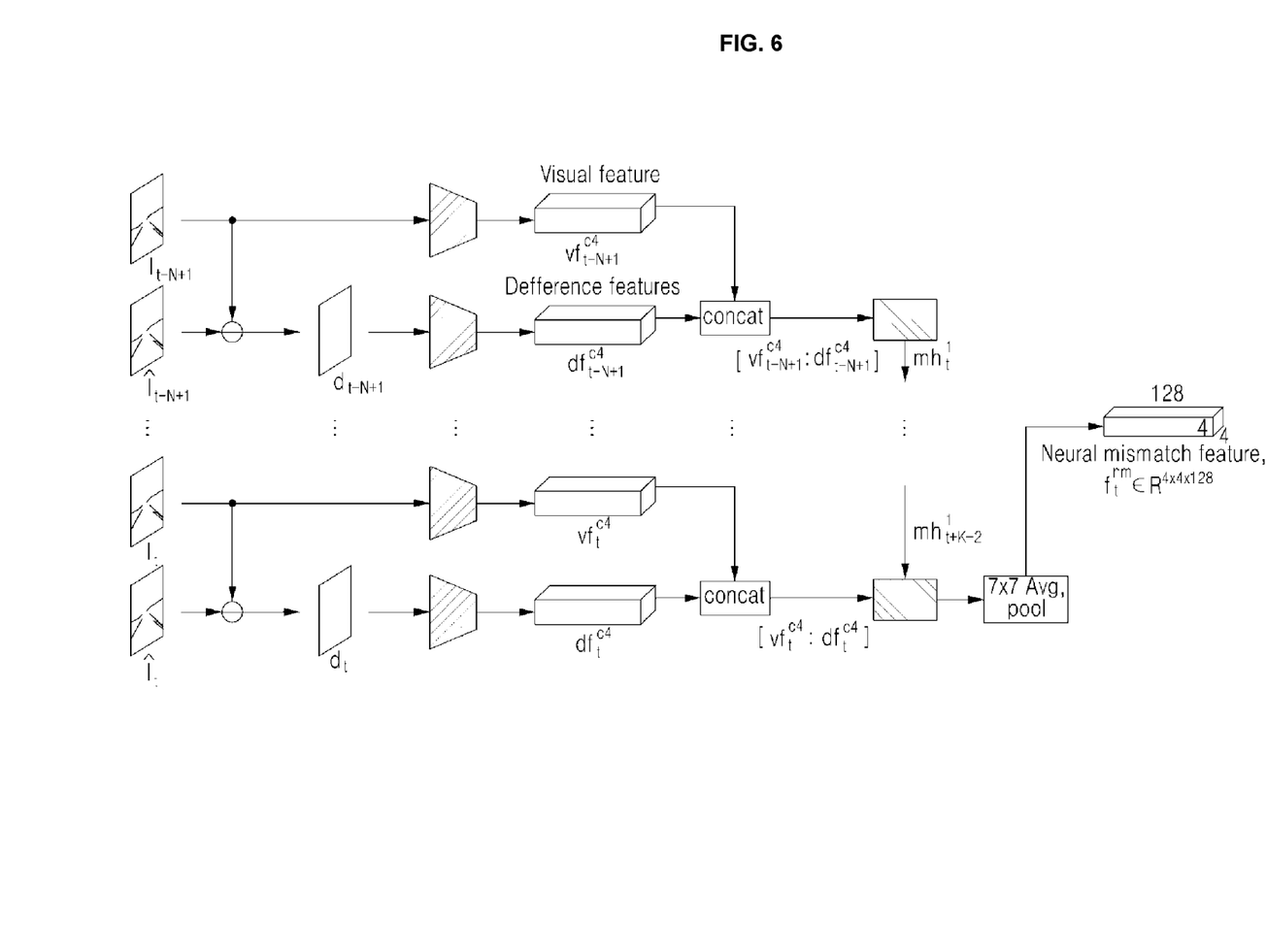
FIG. 6 illustrates an architecture of one embodiment for a deep comparison network.

FIG. 6 illustrates an architecture of one embodiment for a deep comparison network, where the light blue box represents CNN and the yellow box represents ConvLSTM.

The deep comparison network illustrated in FIG. 6 may be a network for encoding a neural mismatch feature. After a predicted video is obtained by the trained deep neural store network, visual information of an input video sequence as well as difference information between an original frame and a predicted frame may be encoded. The difference dt between the original frame, that is, the visual sensory input and the predicted frame, may be expressed as Equation 5 below.

$$d_t = |I_t - P_\theta)I_{t-N}, \ldots, I_{t-1})| = |I_t - \hat{I}_t| \quad \text{[Equation 5]}$$

The difference map $d_t$ may represent a difference between the visual sensory input sensed by a user's eye and the visual signal expected in the experience of the user's neural store, and a difference map for such VR content may be generated and provided. Visual information may be also important factors affecting motion sickness. Therefore, to accurately predict the level of VR sickness, the inventive concept may consider both the visual information of the input video and the difference information between the original video and the predicted video. In this regard, the feature map of the fourth convolutional layer of VGG-19 (K. Simonyan and A. Zisserman, "Very deep convolutional networks for large-scale image recognition," arXiv preprint arXiv: 1409.1556, 2014.) may be used as the visual feature and the difference feature expressed by $vf^{c4} \in \mathbb{R}^{56 \times 56 \times 128}$ and $df^{c4} \in \mathbb{R}^{56 \times 56 \times 128}$. $f_{mn} \in \mathbb{R}^{4 \times 4 \times 128}$ may represent a neural mismatch feature. The visual feature and the difference feature obtained after obtaining $vf^{c4}$ and $df^{c4}$ are concatenated as shown in FIG. 5. The concatenated feature $[vf^{c4}; df^{c4}]$ may be finally encoded using a spatio-temporal encoder using ConvLSTM to obtain the $f^{mn}$ that is a neural mismatch feature. Of course, the concatenated feature encoded by the spatio-temporal encoder may provide the neural mismatch feature $f^{mn}$ through the average pool layer, thereby obtaining the neural mismatch feature in a corresponding network.

Table 3 below shows the architecture of the spatio-temporal encoder to obtain the neural mismatch feature.

TABLE 3

| Layer | Filter/Stride | Output size (W × H × C) |
|---|---|---|
| ConvLSTM 1 | 3 × 3/(2, 2) | 56 × 56 × 256 |
| ConvLSTM 2 | 3 × 3/(2, 2) | 28 × 28 × 128 |
| ConvLSTM 3 | 3 × 3/(2, 2) | 14 × 14 × 128 |

Figure 7:
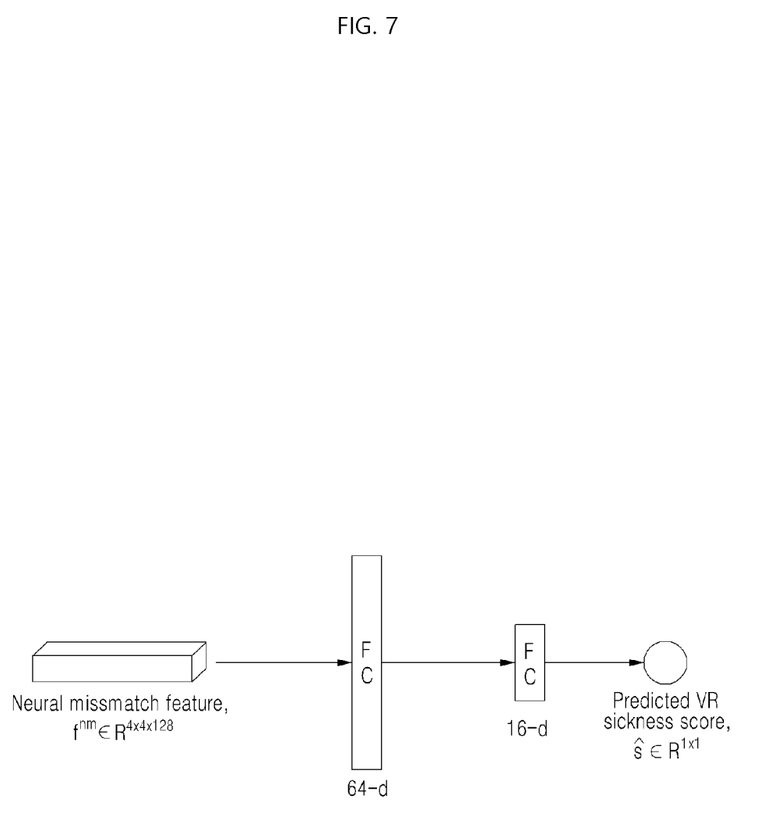
FIG. 7 illustrates an architecture of one embodiment for a deep VR sickness score prediction network.

FIG. 7 illustrates an architecture of one embodiment for a deep VR sickness score prediction network, where the deep VR sickness score prediction network may assess a level of VR sickness due to a latent neural mismatch feature.

As shown in FIG. 7, the deep VR sickness score prediction network may include three fully connected layers, for example a 64-dimensional layer, a 16-dimensional layer and a 1-dimensional layer. The deep VR sickness score prediction network may serve to nonlinearly map a high dimensional neural mismatch feature space onto a low dimensional VR sickness score space. To this end, the VR sickness score in the training process may be predicted from the latent neural mismatch feature $f^{mn}$ by minimizing an objective function between a predicted score and a ground truth subjective score.

Here, the inventive concept may use an average total SSQ score value obtained in the subjective assessment experiment as the ground-truth VR sickness score.

The objective function $L_{score}$ of the deep comparison network and the VR sickness score network for prediction of the VR sickness score may be expressed as Equation 6 below.

$$L_{score} = \frac{1}{K}\sum_{j=1}^{K}\|f_{VRSP}(f^{mn}) - SSQ_j^{total}\|_2^2 \quad \text{[Equation 6]}$$

where $f_{VRSP}()$ may represent nonlinear regression by the fully connected layer, $f_{VRSP}(f^{mn})$ may represent the predicted VR sickness score, $SSQ_j^{total}$ may represent the ground truth subjective score of the j-th VR content, and K may represent the number of placements.

First, the video frames expected in the test process may be obtained by the trained deep neural store network. Then, the VR sickness score may be obtained from the original video sequence and the expected video sequence through the trained deep comparison network and the VR sickness score prediction network.

As described above, the method according to the embodiment of the inventive concept may model the neural mismatch phenomenon that the VR sickness is felt when viewing VR content using deep learning, and quantitatively predict the VR sickness in consideration of the modeled neural mismatch model.

That is, the method according to the embodiment of the inventive concept may quantitatively predict a level of VR sickness using the deep network obtained by modeling a phenomenon in which motion sickness is caused due to mismatch between an input sensory signal sensed when viewing VR content and an expected sensory signal predicted by a neural store with past experiences.

Furthermore, the method according to the embodiment of the inventive concept may generate and provide a difference map corresponding to the difference information between the input visual signal and the expected visual signal for each frame with respect to VR content to be evaluated, so that the difference map may be referred to in the case of producing VR content, and may provide VR sickness information on VR content in the case of providing the VR content to a user by providing a VR assessment score.

Figure 8:
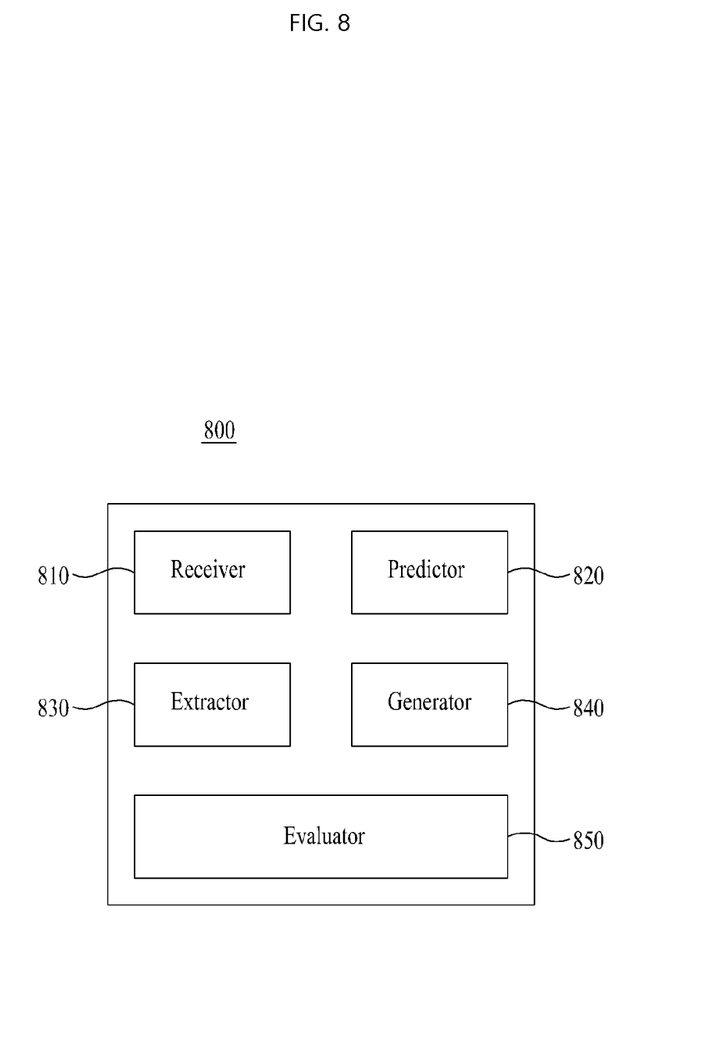
FIG. 8 illustrates a configuration of a virtual reality sickness assessment apparatus according to an embodiment of the inventive concept.

FIG. 8 illustrates a configuration of a virtual reality sickness assessment apparatus according to an embodiment of the inventive concept.

Referring to FIG. 8, an apparatus 800 according to an embodiment of the inventive concept may include a receiver 810, a predictor 820, an extractor 830, a generator 840, and an evaluator 850.

The receiver 810 may receive VR content to be evaluated for a level of VR sickness.

The predictor 820 may predict an expected visual signal for an input visual signal of the VR content by using a first neural network based on a pre-trained first learning model.

The extractor 830 may extract a neural mismatch feature between the expected visual signal predicted and the input visual signal of a corresponding frame of the VR content corresponding to the expected visual signal using a second neural network based on a pre-trained second learning model.

In this case, the extractor 830 may extract the neural mismatch feature based on difference information between the predicted expected visual signal and the input visual signal for the corresponding frame, or may extract the neural mismatch feature based on a difference feature and a visual feature obtained after obtaining a difference feature for the difference information between the expected visual signal predicted and the input visual signal for a corresponding frame and the visual feature for the input visual signal for the corresponding frame.

The generator 840 may generate a difference map for the VR content based on the difference information between the expected visual signal predicted for each frame of the VR content and the input visual signal for the corresponding frame of the VR content corresponding to the expected visual signal.

The evaluator 850 may evaluate the level of VR sickness corresponding to the extracted neural mismatch feature using a third neural network based on a pre-third trained learning model.

In this case, the evaluator 850 may evaluate the level of VR sickness by providing a VR sickness score for the VR content.

The first learning model, the second learning model, and the third learning model may be modeled by a neural mismatch model, and be trained based on SSQ scores evaluated for a preset dataset and pieces of VR content included in the dataset, and thus the first learning model, the second learning model, and the third learning model corresponding to the neural mismatch model may be formed.

FIG. 8 is an apparatus for evaluating VR sickness of VR content using three neural networks, and the apparatus of the inventive concept may evaluate the VR sickness of the VR content using a single neural network.

For example, the apparatus according to another embodiment of the inventive concept may include a receiver, an evaluator, and a generator. The receiver may receive VR content to be evaluated for the level of VR sickness, and the evaluator may quantitatively evaluate VR sickness for VR content using a neural network based on a pre-trained neural mismatch model.

Here, the evaluator may predict an expected visual signal for an input visual signal of the VR content based on the neural mismatch model, extract a neural mismatch feature between the expected visual signal predicted and the input visual signal for a corresponding frame of the VR content corresponding to the expected visual signal, and evaluate a level of VR sickness based on the extracted neural mismatch feature.

Furthermore, the evaluator may extract the neural mismatch feature based on difference information between the predicted expected visual signal and the input visual signal for the corresponding frame, or may extract the neural mismatch feature based on a difference feature and a visual feature obtained after obtaining a difference feature for the difference information between the expected visual signal predicted and the input visual signal for a corresponding frame and the visual feature for the input visual signal for the corresponding frame.

The neural network may be trained based on a dataset including pieces of preset VR content and an SSQ score evaluated for each of the pieces of VR content and thus, a learning model of the neural mismatch model may be formed.

The generator may generate a difference map for the VR content based on the difference information between the expected visual signal predicted for each frame of the VR content and the input visual signal for the corresponding frame of the VR content corresponding to the expected visual signal.

Although the description is omitted with reference to the apparatus of FIG. 8 and the apparatus described above, components constituting FIG. 8 may include all the contents described with reference to FIGS. 1 to 7, which are obvious to those skilled in the art.

The apparatus described herein may be implemented with hardware components and software components and/or a combination of the hardware components and the software components. For example, the apparatus and components described in the embodiments may be implemented using one or more general-purpose or special purpose computers, such as, for example, a processor, a controller, an arithmetic logic unit (ALU), a digital signal processor, a microcomputer, a field programmable array (FPA), a programmable logic unit (PLU), a microprocessor or any other device capable of executing and responding to instructions. The processing device may run an operating system (OS) and one or more software applications that run on the OS. The processing device also may access, store, manipulate, process, and create data in response to execution of the software. For convenience of understanding, one processing device is described as being used, but those skilled in the art will appreciate that the processing device includes a plurality of processing elements and/or multiple types of processing elements. For example, the processing device may include multiple processors or a single processor and a single controller. In addition, different processing configurations are possible, such a parallel processors.

The software may include a computer program, a piece of code, an instruction, or some combination thereof, for independently or collectively instructing or configuring the processing device to operate as desired. Software and data may be embodied in any type of machine, component, physical or virtual equipment, computer storage medium or device to provide instructions or data to or to be interpreted by the processing device. The software also may be distributed over network coupled computer systems so that the software is stored and executed in a distributed fashion. In particular, the software and data may be stored by one or more computer readable recording mediums.

The above-described methods may be embodied in the form of program instructions that can be executed by various computer means and recorded on a computer-readable medium. The computer readable medium may include program instructions, data files, data structures, and the like, alone or in combination. Program instructions recorded on the media may be those specially designed and constructed for the purposes of the present invention, or they may be of the kind well-known and available to those having skill in the computer software arts. Examples of computer readable recording media include magnetic media such as hard disks, floppy disks and magnetic tape, optical media such as CD-ROMs, DVDs, and magnetic disks such as floppy disks, Magneto-optical media, and hardware devices specifically configured to store and execute program instructions, such as ROM, RAM, flash memory, and the like. Examples of program instructions include not only machine code generated by a compiler, but also high-level language code that can be executed by a computer using an interpreter or the like.

Although the embodiments have been described by the limited embodiments and the drawings as described above, various modifications and variations are possible to those skilled in the art from the above description. For example, the described techniques may be performed in a different order than the described method, and/or components of the described systems, structures, devices, circuits, etc. may be combined or combined in a different form than the described method, or other components, or even when replaced or substituted by equivalents, an appropriate result can be achieved.

Therefore, other implementations, other embodiments, and equivalents to the claims are within the scope of the following claims.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A virtual reality (VR) sickness assessment method, comprising:
   receiving virtual reality content; and
   quantitatively evaluating virtual reality sickness for the received virtual reality content using a neural network based on a pre-trained neural mismatch model that is trained by performing hostile learning between a spatio-temporal predictor and a spatio-temporal discriminator, wherein the evaluating of the virtual reality sickness includes:
      predicting an expected visual signal for an input visual signal of the virtual reality content based on the neural mismatch model;
      extracting a neural mismatch feature between the predicted expected visual signal based on the neural mismatch model and an input visual signal for a corresponding frame of the virtual reality content corresponding to the expected visual signal; and
      evaluating a level of the virtual reality sickness based on the neural mismatch model and the extracted neural mismatch feature.

2. The virtual reality sickness assessment method of claim 1, wherein the extracting of the neural mismatch feature includes extracting the neural mismatch feature based on difference information between the predicted expected visual signal and the input visual signal for the corresponding frame.

3. The virtual reality sickness assessment method of claim 1, wherein the extracting of the neural mismatch feature includes obtaining a difference feature for difference information between the predicted expected visual signal and the input visual signal for the corresponding frame and a visual feature for the input visual signal for the corresponding frame and extracting the neural mismatch feature based on the difference feature and the visual feature.

4. The virtual reality sickness assessment method of claim 1, wherein the evaluating of the virtual reality sickness further includes generating a difference map for the virtual reality content based on difference information between the expected visual signal predicted for each frame of the virtual reality content and the input visual signal for the corresponding frame of the virtual reality content corresponding to the expected visual signal.

5. The virtual reality sickness assessment method of claim 1, wherein the neural network is trained based on a dataset including pieces of preset virtual reality content and a simulator sickness questionnaire (SSQ) score evaluated for each of the pieces of virtual reality content to form a learning model of the neural mismatch model.

6. A virtual reality sickness assessment (VRSA) method, comprising:
receiving virtual reality content; and
predicting an expected visual signal for an input visual signal of the VR content by using a first neural network based on a pre-trained first learning model that is trained by performing hostile learning between a spatio-temporal predictor and a spatio-temporal discriminator;
extracting a neural mismatch feature between the expected visual signal predicted and the input visual signal of a corresponding frame of the virtual reality content corresponding to the expected visual signal using a second neural network based on a pre-trained second learning model; and
evaluating a level of virtual reality sickness corresponding to the extracted neural mismatch feature using a third neural network based on a pre-third trained learning model,
wherein a neural mismatch model is formed by the first learning model, the second learning model, and the third learning model.

7. The virtual reality sickness assessment method of claim 6, wherein the extracting of the neural mismatch feature includes extracting the neural mismatch feature based on difference information between the predicted expected visual signal and the input visual signal for the corresponding frame.

8. The virtual reality sickness assessment method of claim 6, wherein the extracting of the neural mismatch feature includes obtaining a difference feature for difference information between the predicted expected visual signal and the input visual signal for the corresponding frame and a visual feature for the input visual signal for the corresponding frame and extracting the neural mismatch feature based on the difference feature and the visual feature.

9. The virtual reality sickness assessment method of claim 6, further comprising:
generating a difference map for the virtual reality content based on difference information between the expected visual signal predicted for each frame of the virtual reality content and the input visual signal for the corresponding frame of the virtual reality content corresponding to the expected visual signal.

10. A virtual reality sickness assessment (VRSA) apparatus, comprising:
a receiver configured to receive virtual reality content; and
an evaluator configured to quantitatively evaluate virtual reality sickness for the received virtual reality content using a neural network based on a pre-trained neural mismatch model that is trained by performing hostile learning between a spatio-temporal predictor and a spatio-temporal discriminator, wherein the evaluator is configured to:
predict an expected visual signal for an input visual signal of the virtual reality content based on the neural mismatch model;
extract a neural mismatch feature between the predicted expected visual signal based on the neural mismatch model and an input visual signal for a corresponding frame of the virtual reality content corresponding to the expected visual signal; and
evaluate a level of the virtual reality sickness based on the neural mismatch model and the extracted neural mismatch feature.

11. The virtual reality sickness assessment apparatus of claim 10, wherein the evaluator extracts the neural mismatch feature based on difference information between the predicted expected visual signal and the input visual signal for the corresponding frame.

12. The virtual reality sickness assessment apparatus of claim 10, wherein the evaluator obtains a difference feature for difference information between the predicted expected visual signal and the input visual signal for the corresponding frame and a visual feature for the input visual signal for the corresponding frame and extracts the neural mismatch feature based on the difference feature and the visual feature.

13. The virtual reality sickness assessment apparatus of claim 10, further comprising:
a generator configured to generate a difference map for the virtual reality content based on difference information between the expected visual signal predicted for each frame of the virtual reality content and the input visual signal for the corresponding frame of the virtual reality content corresponding to the expected visual signal.

14. The virtual reality sickness assessment apparatus of claim 10, wherein the neural network is trained based on a dataset including pieces of preset virtual reality content and a simulator sickness questionnaire (SSQ) score evaluated for each of the pieces of virtual reality content to form a learning model of the neural mismatch model.

15. A virtual reality sickness assessment (VRSA) apparatus, comprising:
a receiver configured to receive virtual reality content; and
a predictor configured to predict an expected visual signal for an input visual signal of the VR content by using a first neural network based on a pre-trained first learning model that is trained by performing hostile learning against a discriminator;
an extractor configured to extract a neural mismatch feature between the expected visual signal predicted and the input visual signal of a corresponding frame of the VR content corresponding to the expected visual signal using a second neural network based on a pre-trained second learning model; and
an evaluator configured to evaluate a level of virtual reality sickness corresponding to the extracted neural mismatch feature using a third neural network based on a pre-third trained learning model,
wherein a neural mismatch model is formed by the first learning model, the second learning model, and the third learning model.

16. The virtual reality sickness assessment apparatus of claim 15, wherein the extractor extracts the neural mismatch feature based on difference information between the predicted expected visual signal and the input visual signal for the corresponding frame.

17. The virtual reality sickness assessment apparatus of claim 15, wherein the extractor obtains a difference feature for difference information between the predicted expected visual signal and the input visual signal for the corresponding frame and a visual feature for the input visual signal for the corresponding frame and extracts the neural mismatch feature based on the difference feature and the visual feature.

18. The virtual reality sickness assessment apparatus of claim 15, further comprising:
   a generator configured to generate a difference map for the virtual reality content based on difference information between the expected visual signal predicted for each frame of the virtual reality content and the input visual signal for a corresponding frame of the virtual reality content corresponding to the expected visual signal.

* * * * *